United States Patent [19]

Avar

[11] Patent Number: 4,859,725
[45] Date of Patent: Aug. 22, 1989

[54] OXALAMIDE COMPOUNDS USEFUL AS UV ABSORBERS

[75] Inventor: Lajos Avar, Biel-Benken, Switzerland

[73] Assignee: Sandoz Ltd., Basel, Switzerland

[21] Appl. No.: 236,075

[22] Filed: Aug. 23, 1988

Related U.S. Application Data

[63] Continuation-in-part of Ser. No. 117,774, Nov. 5, 1987, abandoned.

[30] Foreign Application Priority Data

Nov. 7, 1986 [GB] United Kingdom ............... 8626608

[51] Int. Cl.$^4$ .................... C08K 5/34; C08K 5/20; C07C 103/46; C07D 249/20; C07D 211/98
[52] U.S. Cl. ........................... 524/91; 524/99; 524/219; 546/199; 548/261; 560/19; 560/48
[58] Field of Search .................. 524/91, 99, 219; 546/199; 548/261; 560/19, 48

[56] References Cited

U.S. PATENT DOCUMENTS

| | | | |
|---|---|---|---|
| 3,529,982 | 9/1970 | Luethi et al. | 524/219 |
| 3,906,033 | 9/1975 | Biland et al. | 524/219 |
| 3,954,706 | 5/1976 | Wang et al. | 548/261 |
| 4,061,652 | 12/1977 | Schroeter et al. | 548/261 |
| 4,166,803 | 9/1979 | Frick et al. | 524/91 |
| 4,289,686 | 9/1981 | Rody | 546/91 |
| 4,414,393 | 11/1983 | Dexter et al. | 548/259 |
| 4,504,628 | 3/1985 | Johnson | 548/259 |
| 4,645,853 | 2/1987 | Stephen et al. | 524/219 |

Primary Examiner—Veronica P. Hoke
Attorney, Agent, or Firm—Gerald D. Sharkin; Richard E. Vila; Thomas C. Doyle

[57] ABSTRACT

A compound of formula I

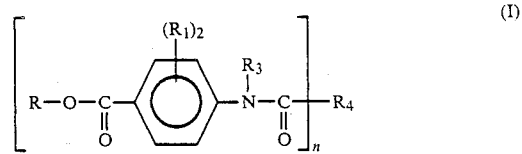

in which R to $R_5$ are organic radicals, for use as a light stabilizer in polymeric systems.

20 Claims, No Drawings

OXALAMIDE COMPOUNDS USEFUL AS UV ABSORBERS

This application is a continuation-in-part of U.S. Ser. No. 117,774, filed on Nov. 5th, 1987 and now abandoned.

The invention relates to novel oxalamide compounds, suitable for use as U.V. absorbers.

According to the invention, there is provided a compound of formula I

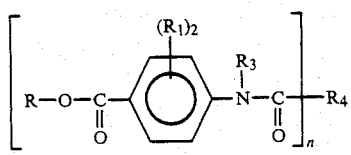

in which n is 1 or 2;

R is a phenyl group substituted by a benztriazolyl or benzoyl group;

each $R_1$, independently, is hydrogen, $C_{1-8}$alkyl, $C_{1-8}$alkoxy or halogen;

$R_3$ is hydrogen or $C_{1-4}$alkyl;

$R_4$, when n=2, is a direct bond; and when n=1, is

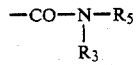

where $R_5$ is an unsubstituted or substituted phenyl group; a $C_{1-22}$alkyl; or a 4-(2,2,6,6-tetra-$C_{1-4}$alkyl piperidinyl) group.

For the avoidance of doubt, in R the phenyl group may be further substituted, for example by one or two groups selected from $C_{1-22}$alkyl, $C_{1-22}$alkoxy and halogen groups and the benztriazolyl or benzophenone group present may be substituted, for example by one, two or three groups selected from $C_{1-22}$alkyl, $C_{1-22}$alkoxy and halogen.

Preferred compounds of formula I are of formula II or III

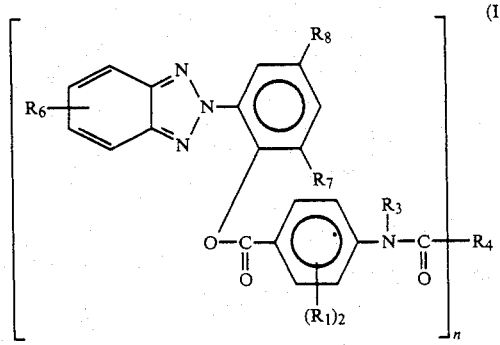

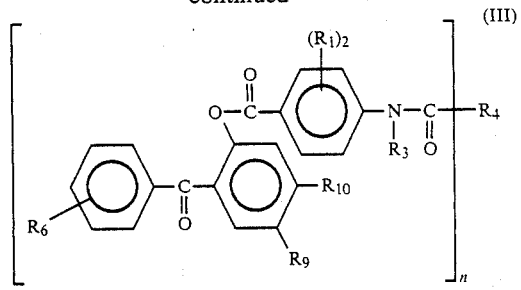

in which $R_6$ is hydrogen, $C_{1-8}$alkyl, $C_{1-8}$alkoxy, $C_{1-4}$alkyl phenyl or halogen;

$R_7$ is hydrogen or $C_{1-22}$alkyl;

$R_8$ is hydrogen, $C_{1-22}$alkyl or phenyl($C_{1-22}$alkyl);

$R_9$ is hydrogen, $C_{1-22}$alkyl or $C_{1-22}$alkoxy;

$R_{10}$ is hydrogen, $C_{1-22}$alkyl or $C_{1-22}$alkoxy; and the remaining symbols are as defined above.

More preferred compounds of formula I are of formula II.

In this specification any group capable of being linear or branched is linear or branched. In this specification where a symbol appears more than once in a formula, its significances are independent of one another.

Preferably $R_1$ is $R_1'$ where $R_1'$ is hydrogen or methyl, more preferably hydrogen.

Preferably $R_3$ is $R_3'$ where $R_3'$ is hydrogen or methyl, more preferably hydrogen.

Preferably $R_4$ is $R_4'$ where $R_4'$ is a direct bond when n=2 or, when n=1, is

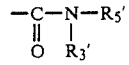

where $R_5'$ is $C_{1-22}$alkyl, phenyl, unsubstituted or mono-, di- or tri-substituted by groups selected from $C_{1-12}$alkyl, $C_{1-12}$alkoxy, and halogen; or $R_5'$ is

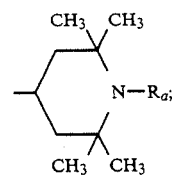

$R_3'$ is as defined above and $R_a$ is hydrogen, oxygen, $C_{1-8}$alkyl or —CO—$R_{15}$ where $R_{15}$ is —C($R_3$)=$CH_2$, $C_{1-6}$alkyl, phenyl, —CO—O—$C_{1-4}$alkyl or —$NR_{17}R_{18}$ where $R_{17}$ is hydrogen, $C_{1-12}$alkyl, $C_{5-6}$cycloalkyl, phenyl, phenyl $C_{1-4}$alkyl or $C_{1-12}$alkylphenyl and $R_{18}$ is $C_{1-12}$alkyl or hydrogen.

Preferably $R_6$ is $R_6'$ where $R_6'$ is hydrogen, methyl, ethyl, $C_8H_{17}$, methoxy, ethoxy or chloro, more preferably $R_6$ is $R_6''$ where $R_6''$ is methyl, ethyl or hydrogen.

Preferably $R_7$ is hydrogen.

Preferably $R_8$ is $R_8'$ where $R_8'$ is $C_{1-22}$alkyl, more preferably $R_8$ is $R_8''$ where $R_8''$ is $C_{1-18}$alkyl, most preferably $R_8$ is $R_8'''$ where $R_8'''$ is $C_{1-12}$alkyl. Preferably $R_9$ is $R_9'$ where $R_9'$ is $C_{1-22}$alkyl or $C_{1-22}$alkoxy, more preferably $R_9$ is $R_9''$ where $R_9''$ is $C_{1-4}$alkyl or $C_{1-4}$alkoxy.

Preferably $R_{10}$ is $R_{10}'$ where $R_{10}'$ is $C_{1-8}$alkoxy, more preferably $R_{10}$ is $R_{10}''$ where $R_{10}''$ is $C_{4-8}$alkoxy.

Preferably any $C_{1-12}$alkyl group is a $C_{1-8}$alkyl group; any $C_{1-8}$alkyl is preferably a $C_{1-4}$alkyl group; and preferably any $C_{1-4}$alkyl group is methyl or ethyl. Any $C_{1-4}$alkoxy is preferably methoxy or ethoxy and any halogen is preferably chloro or bromo, more preferably chloro.

Further, according to the invention, there is provided a process for preparing a compound of formula I, where n=1, comprising reacting one mole of a compound of formula IV

R—OH (IV)

with one mole of a compound of formula V

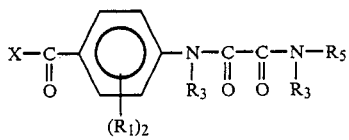

where X is halogen, and the other symbols are defined above: at an elevated temperature.

Further, according to the invention, there is provided a process for preparing a compound of formula I where n=2, comprising reacting two moles of a compound of formula IV defined above with one mole of a compound of formula VI

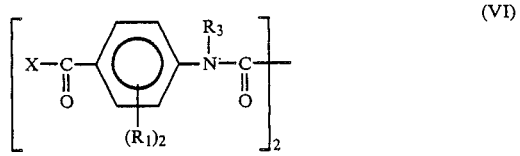

where X is halogen and the other symbols are as defined above, at an elevated temperature.

Compounds of formula IV, V and VI are known or can be prepared by known methods from known compounds.

Preferably in the processes of the invention the temperature of the reaction is between 90° C. and 150° C., more preferably 100°–120° C. Preferably the pH of the reaction is from 7 to 9.

Further, according to the invention, there is provided a polymeric composition comprising a polymeric material and a compound of formula I.

The concentration of compound of formula I employed in the polymeric material is suitably 0.01 to 8% by weight, preferably 0.02 to 1% by weight. The compound may be added before, during or after the polymerization step, and may be added in solid form; in solution, preferably as a liquid concentrate containing from 20 to 80% by weight of compound of formula I; or as a solid masterbatch composition containing 20 to 80% by weight of compound of formula I and 80 to 20% by weight of a solid polymeric material which is identical with or compatible with the polymeric material to be stabilized.

Still, further according to the invention, there is provided a process for stabilizing a polymeric substrate comprising adding to the substrate a light stabilising amount of a compound of formula I defined above.

Compounds of formula I are useful as stabilizers to protect polymeric materials against degradation by light. The compounds have particularly good solubility and miscibility in solvent systems and in liquid polymers and prepolymers, which makes them useable in a wide range of polymeric materials.

Suitable polymeric materials include plastics materials for example polyethylene, polypropylene, ethylene/propylene copolymers, polyvinyl chloride, polyester, polyamide, polyurethane, polyacrylonitrile, poly(acrylonitrile-butadiene-styrene) terpolymers of acrylates, styrene and acrylonitrile, styrene/acrylonitrile and styrene/butadiene. Other plastics materials such as polybutylene, polystyrene, chlorinated polyethylene, polycarbonate, polymethylmethacrylate, polyphenylene oxide, polypropylene oxide, polyacetals, phenol/fonmaldehyde resins and epoxy resins may also be used. Preferred plastics materials are polypropylene, polyethylene, ethylene/propylene copolymers and ABS. Natural polymers for example natural rubber may also be stabilized, as may lubricating oils containing polymeric material.

The compounds of formula I may be incorporated by known methods into the polymeric material to be stabilized. Of particular importance is blending of the compounds with thermoplastic polymers in the melt, for example in a melt blender or during the formation of shaped articles, including foils, films, tubes, containers, bottles, fibres and foams by extrusion, injection moulding, blow moulding, spinning or wire coating.

It is not essential for the polymeric material to be fully polymerised before mixing with the compounds according to the invention. The compounds may be mixed with monomer, prepolymer or precondensate, and the polymerisation or condensation reaction carried out subsequently. This will of course be the preferred method of incorporation of the compounds into thermosetting polymers, which cannot be melt blended.

Further, according to the invention, there is provided a lacquer composition based on acrylic, alkyd, polyester and/or polyurethane resins (which, if desired, can be crosslinked with melamine/formaldehyde resins, epoxide resins or polyisocyanates) containing one or more compounds of formula I.

The compounds of formula I may be used alone or in combination with other stabilizers, for example hindered amine light stabilizers such as 2,2,6,6-tetraalkylpiperidine light stabilizers (e.g. N-unsubstituted or N-alkyl or N-acyl substituted 2,2,6,6-tetramethylpiperidine compounds) and antioxidants.

Compounds of formula I with hindered amine light stabilizers may produce a synergistic effect in polymeric systems. Preferred hindered amine light stabilizers are those described in U.S. Pat. No. 4,408,051 and GB Patent No. 2,091,732 B, the contents of both patents (including their preferences) are incorporated herein by reference. Examples of other stabilizers include sterically hindered phenols, sulphur or phosphorus-containing compounds or mixtures of these. More specific examples of these other stabilizers are benzofuran-2-ones; indolin-2-ones and sterically hindered phenols such as indolin-2-ones and sterically hindered phenols such as beta-(4-hydroxy-3,5-ditert.-butylphenyl)-propionyl stearate, methane tetrakis(methylene-3(3', 5'-ditert.-butyl-4-hydroxy-phenyl-)-propionate), 1,3,3-tris-(2-methyl-4-hydroxy-5-tert.-butyl phenyl)-butane, 1,3,5-tris(4-tert.-butyl-3-hydroxy-2,6-dimethylbenzyl)-1,3,5-triazin-2,4,6 (1H, 3H, 5H)-trione, bis-(4-tert.-butyl-3-hydroxy-2,6-dimethylbenzyl)dithiolterephthalate, tris(3,5-ditert.-butyl-4-hydroxybenzyl) isocyanurate, the triester of (4-hydroxy-3,5-ditert.-butyl-phenyl) propionic acid with 1,3,4-tris-(2-hydroxyethyl)-5-triazin-2,4,6 (1H, 3H, 5H)-trione, bis-[3,3-bis-(4'-hydroxy-3-tert.-butyl-phenyl)-butyricacid] glycol ester, 1,3,5-trimethyl-2,4,6tris-(3,5-ditert.-butyl-4 1-hydroxy-phenyl) benzene, 2,2'-methylene-bis-(4-methyl-6-tert.-butyl-phenyl) terephthalate, 4,4-methylene-bis-(2,6-ditert.-butylphenol), 4,4'-butylidine-bis-(tert.-butylmetacresol), 2,2'-methylene-bis-(4-methyl-6-tert.-butyl-phenol).

Sulphur-containing antioxidative co-stabilizers which may be used include for example distearylthiodipropionate, di-laurylthiodipropionate, methane tetrakis (methylene-3-hexylthiopropionate), methane tetrakis (methylene-3-dodecylthiopropionate)and dioctadecyl-disulphide. Phosphorus-containing co-stabilizers include for example trinonylphenyl phosphite, 4,9-distearyl-3,5,8,10-tetraoxadiphosphaspiroundecane, tris-(2,4-ditert.butylphenyl)phosphite and tetrakis (2,3-ditert.-butylphenyl)-4,4'-biphenylene diphosphonite. Further additives such as aminoaryl compounds and U.V.-absorbers and light stabilizers e.g. 2-(2'-hydroxyphenyl)-benzotriazole, 2-hydroxybenzophenone, 1,3-bis-(2'-hydroxybenzoyl)benzene, salicylates, cinnamates, benzoates and substituted benzoates, sterically hindered amines and oxalic acid diamides may be used. Other known types of additives, e.g. flame retardants and antistatic agents, may also be added.

The compounds of the invention can also be used in photopolymeric substrates containing photoinitiators for the photopolymerisation.

The compounds of formula I are especially suitable for use in organic polymer-containing coatings, particularly automotive finishes.

Automotive finishes are generally solutions or dispersions of organic polymers or polymer precursors in organic solvents. The majority are stoving finishes, which require the application of heat, generally above 80° C., in order to harden the finish in an acceptable time once it has been applied to the primer-coated metal surface. The hardening step may be accelerated by the use of an acid catalyst. The effect of this heating may be to accelerate the chemical reaction between polymer precursors in a thermosetting system, or to bring about fusion of particles of a thermoplastic polymer.

Many automotive finishes are metallic finishes, which contain flakes of metal, usually aluminium, in order to provide optical effects due to reflection. Such finishes are often two-coat finishes, in which a clear top coat finish is applied over a base coat finish containing a single pigment and/or metal flakes. The compounds of formula I can be in the top coat finish or the ground coat finish, preferably the former. Such two-coat metallic finishes have particular need of U.V.-stabilizers in the top coat, since the polymer in this coat is not protected by light-absorbing pigments, and it is subjected to almost double the normal amount of radiation because of reflection of light from the lower metallic layer.

The compounds of formula I are suitable for use as U.V.-stabilizers in a wide range of liquid finishes, for example those based on combinations of melamine-formaldehyde resins with oil-modified polyester resins, polyacrylate resins with added crosslinkers, or saturated polyesters; or on self-crosslinkers, or saturated polyesters; or on self-crosslinked polyacrylate or polyacrylate resin co-polymerised with styrene.

Further examples are two-component finishes based on an aliphatic or aromatic di-isocyanate and a hydroxy-group-containing polyacrylate, polyester or polyether resin. These polyurethane 2-component finishes are preferably hardened at 60° to 120° C. Thermoplastic polyacrylate resins may also be used, the latter being particularly useful in metallic finishes, as are also polyacrylate resins with added crosslinkers in combination with melamine-fonmaldehyde resins etherified with butanol and, further, hydroxy-group-containing polyacrylate resins hardened with aliphatic di-isocyanates.

The compounds of formula I are particularly useful in acid catalysed stoving finishes particularly in the top coats of two layer metallic finishes.

The compounds of formula I may be added to the finish at any stage in its manufacture, and may be added in solid form or in solution, preferably in the form of a liquid concentrate in a suitable solvent.

In practice, one or more compounds of formula I are added to a liquid finish as a solution in an organic solvent in which liquid finish the binder material is between 35% (low solids liquid finish) and 70% (high solids liquid finish) by weight of the final liquid finish. The binder material of the finish can be in aqueous emulsion or suspension form (aqueous finish) in which typically, the binder material constitutes 20 to 30% by weight of the emulsion or suspension. However, the compounds of formula I can also be added to powder finishes.

The compounds of formula I are to be added to the liquid or powder finishes before stoving or hardening. Preferably the compounds of formula I are used in liquid finishes since it is easy to add exact dosages. It is particularly preferred to use a concentrate (preferably in a hydrocarbon solvent) containing at least 40% preferably 60 to 80% by weight of the total weight of the concentrate of a compound of formula I to introduce the compound of formula I to finishes for stoving.

The addition of from 0.01 to 8% by weight, preferably 0.2 to 4% by weight of one or more compounds of formula I gives a clear improvement in the light- and weather-stability of organic pigments in stoving finishes as well as reducing the tendency to hairline cracking and loss of gloss as the result of weathering. This is also found for metallic finishes and excellent long-term stability of the clear top coat of two layer metallic finishes is obtained. In such finishes, the compound of formula I may be added to the metallic undercoat, the clear top coat or both, preferably only to the clear top coat. The metal surface to be finished may be under-coated with primer coatings as is customary in the art of coating metal surfaces.

The invention will now be illustrated by the following Examples in which all parts are by weight.

EXAMPLE 1

Preparation of the compound of formula 1a

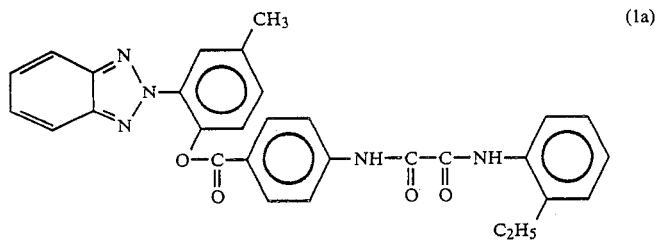

0.02 moles of the compound of the formula 1b

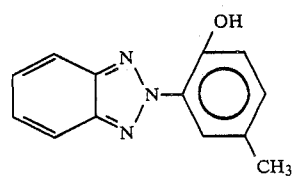

(a compound commercially available as Tinuvin P), 0.02 moles of triethylamine and 0.02 moles of the compound of formula 1c

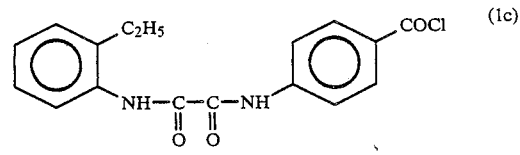

are stirred for 24 hours in toluene at 110° C.

The toluene solution is washed with water and the product is allowed to crystalline out. The resulting product of formula 1a is a white powder having a melting point of 226°–227° C.

EXAMPLE 2

Preparation of a compound of formula 2a

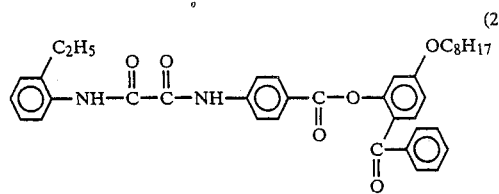

0.02 moles of 2-hydroxy-4-octyloxy-benzophenone, 0.02 moles triethylamine and 0.02 moles of the compound of formula 1c (defined in Example 1) are stirred together in toluene for 22 hours at 110° C. The toluene solution is washed with water, dried and concentration. The residue is crystallised out of isopropanol.

The resulting product of formula 2a is a light beige powder, having a melting point of 131°–132° C.

EXAMPLES 3 AND 4

Examples 1 and 2 are repeated, using instead of 0.02 moles compound of formula 1c, 0.01 moles of the compound of formula 3b

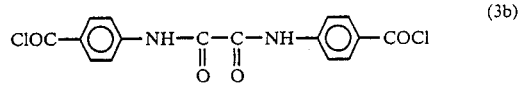

to produce a compound of formula 3a and 4a respectively.

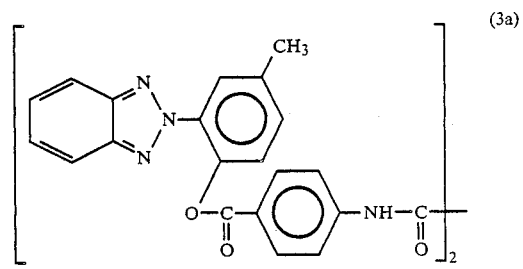

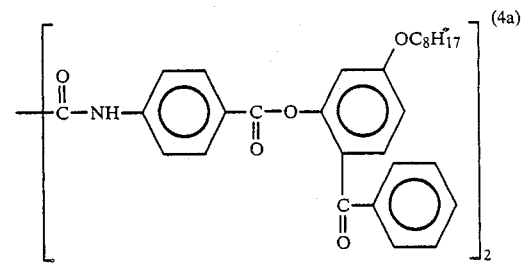

EXAMPLES 5 TO 17

By a method analogous to that of Example 1 from appropriate reactants a compound of the formula

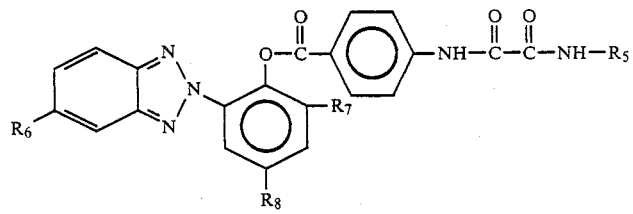

in which $R_5$ to $R_8$ are as defined in Table 1 below, can be prepared.

TABLE 1

| Example No. | R6 | R8 | R5 | R7 |
|---|---|---|---|---|
| 5 | H | C4H9 | C4H9 | H |
| 6 | H | CH3 | C6H13 | CH3 |
| 7 | Cl | C4H9 | C8H17 | C2H5 |
| 8 | H | C5H11 | C12H25 | H |
| 9 | Cl | C5H11 | C18H37 | C2H5 |
| 10 | H | C8H17 | C4H9 | CH3 |
| 11 | Cl | C8H17 | C6H13 | H |
| 12 | Cl | CH3 | C8H17 | C2H5 |
| 13 | C8H17 | C4H9 | C12H25 | CH3 |
| 14 | Cl | C12H25 | C18H37 | C2H5 |
| 15 | CH3 | C12H25 | CH3 | CH3 |
| 16 | Cl | C(CH3)3 | C2H5 | H |
| 17 | H | " | C3H7 | H |

EXAMPLES 18 TO 29

By a method analogous to that of Example 1 from appropriate reactants, compounds of the formula

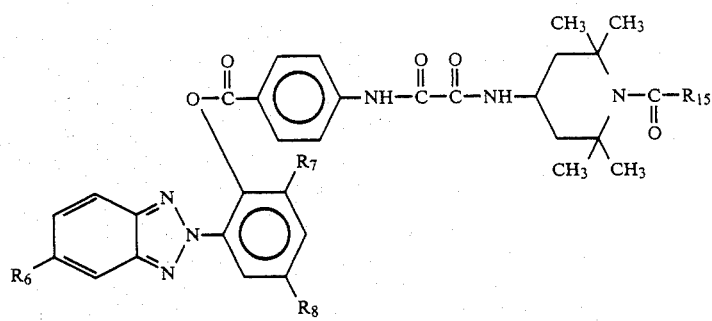

in which R6, R7, R8 and R15 are defined in Table 2 below, can be prepared.

TABLE 2

| Example No. | R6 | R7 | R8 | R15 |
|---|---|---|---|---|
| 18 | H | H | CH3 | CH3 |
| 19 | Cl | H | CH3 | CH3 |
| 20 | OCH3 | H | CH3 | CH3 |
| 21 | C8H17 | H | CH3 | CH3 |
| 22 | H | H | CH3 | C2H5 |
| 23 | H | H | CH3 | C(CH3)3 |
| 24 | H | H | C12H25 | CH3 |
| 25 | Cl | H | C4H9 | CH3 |
| 26 | H | C4H9 | C4H9 | CH3 |
| 27 | H | C5H11 | C5H11 | CH3 |
| 28 | H | H | C8H17 | CH3 |
| 29 | H | H | C6H5—C(CH3)2— | CH3 |

EXAMPLES 30 TO 40

By a method analogous to that of formula 1, from appropriate reactants, compounds of the formula in which R6, R8 and R19 are defined in Table 3 below, can be prepared.

TABLE 3

| Example No. | R6 | R8 | R19 |
|---|---|---|---|
| 30 | H | C8H17 | H |
| 31 | H | C8H17 | OC2H5 |
| 32 | Cl | C4H9 | OC2H5 |
| 33 | C8H17 | C8H17 | OC2H5 |
| 34 | H | C5H11 | H |
| 35 | H | C5H11 | OC2H5 |
| 36 | H | C12H25 | H |
| 37 | H | C12H25 | OC2H5 |
| 38 | H | " | OCH3 |
| 39 | H | " | OC12H25 |
| 40 | Cl | " | OC2H5 |

EXAMPLES 41 TO 43

Compounds of the formula

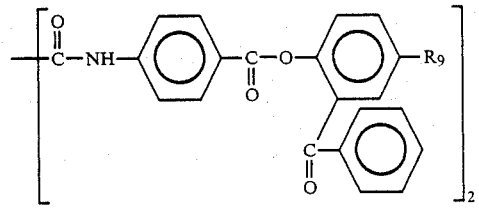

where R9 is defined in Table 4 below; can be prepared from appropriate reactants by the method of Example 1.

TABLE 4

| Example No. | R9 |
|---|---|
| 41 | —OC2H5 |
| 42 | —C2H5 |
| 43 | —C12H25 |

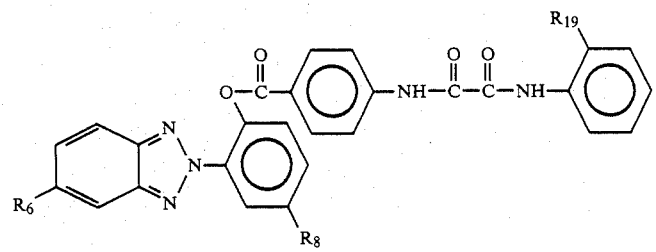

APPLICATION EXAMPLE A

A clear finish of
80 Parts: of Viacryl SC 344 (a 50% solution of an acryl resin from Vianova),
13.9 Parts: of Maprenal MF 80 (a 72% solution of a melamine resin from Hoechst) and
4.1 Parts: of Byketol OK (from Byk-Malinckrodt)
is added to 2 parts of a compound of formula 1a (described in Example 1). After 1 minute the light stabiliser material so formed is dissolved in a finish. The finish is applied conventionally (according to the known 2 layer procedure) to a metallic or single pigment finish whilst still wet by spraying to form a layer having a thickness of 30 to 40 μm. The resulting coating is then hardened at 140° for 30 minutes. The coating shows very good resistance to U.V. light and weathering.

APPLICATION EXAMPLE B

A clear finish of
29.5 Parts: of Setalux C-1502 XX-60 (a 60% solution of an acryl resin from Synthese B.V.),
39.2 Parts: of Setalux C-1382 BX-45 (a 45% solution of an acryl resin from Synthese B.V.),
21.4 Parts: of Setamine US-138 BB-70 (a 70% solution of a melamine resin from Synthese B.V.),
2.5 Parts: of Baysilonoil [(2% solution in Xylene) from Bayer] and
7.4 Parts: of Depanol Y (a solvent from Hoechst)
is stirred together with 2.5 parts of a compound of formula 1a (described in Example 1) and 2 parts of an acid catalyst derived from phosphoric acid (Type: Catalyst 269-9 from American Cyanamid) to form a homogeneous mixture. The finish is applied conventionally (according to known 2 layer procedure) to a metallic or single pigment finish whilst both are still wet by spraying to form a layer having a thickness of 30 to 40 μm. The resulting coating is then hardened at 110° for 20 minutes. The coating shows very good resistance to U.V. light and weathering.

APPLICATION EXAMPLE C

A clear finish of
75: Parts Macrynal SH 510 N (a hydroxy-containing acryl resin from Bayer)
2: Parts of Baysilon-oil A [(1% solution in xylene) from Bayer]
0.3 Parts: of dibutyl zinc dilaurate
0.35 Parts: diethanolamine
5.0 Parts: of ethylglycol acetate
5.0 Parts: of Solvesso 100
6.0 Parts: of Xylene and
6.36 Parts: of butyl acetate
is added to 2.5 parts of a compound of formula 1a (described in Example 1) and 30 parts of Desmodur N 75 (from Bayer). The homogeneous mixture so formed is applied conventionally (according to the known 2 layer procedure) to a metallic or single pigment finish whilst both are still wet by spraying to form a layer having a thickness of 30 to 40 μm and the resulting coating is hardened over 20 minutes at 80° to 90°. The resulting 2K-PUR coating shows a good resistance to U.V. light and weathering.

APPLICATION EXAMPLE D

A single white pigmented finish of
14.30: Parts of Setamine US-132 BB70 (a 70% solution of a melamine resin from Synthese)
57.15: Parts of Setal 84 W-70 (a 70% solution of an alkyd resin from Synthese)
7.70: Parts of n-butanol
1.85: Parts of butylglycol acetate
9.50: parts of Xylene and
25: Parts of titanium dioxide (Rutil type)
is added with 1.38 parts of the product of formula 1a (see Example 1). The finish is conventionally applied to a grounded steel metal to which a filler of layer thickness 20 to 30 μm has been annealed, by spraying and after standing for 30 minutes at room temperature the steel metal surface is annealed at 120° C. for 30 minutes. The resulting coating shows very good resistance to U.V. light and weathering.

In Application Examples A to D instead of the product of formula 1a, an appropriate amount of the product of any one of Examples 2 to 40 may be used.

What is claimed is:

1. A compound of formula I

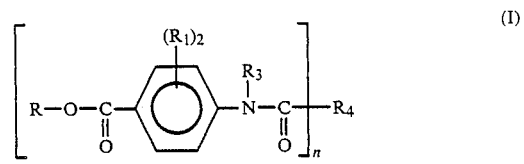

in which
n is 1 or 2;
R is a group of the formula IIa or IIIa

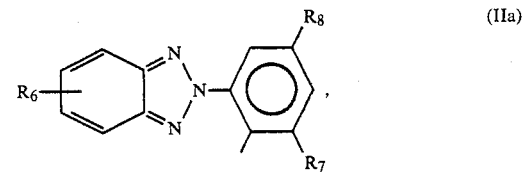

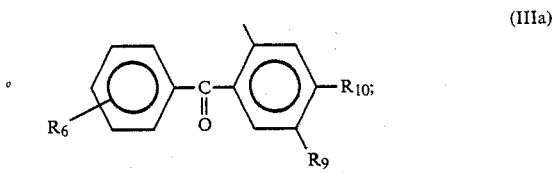

each $R_1$, independently, is hydrogen, $C_{1-8}$alkyl, $C_{1-8}$alkoxy or halogen;
$R_3$ is hydrogen or $C_{1-4}$alkyl;
$R_4$, when n=2, is a direct bond and, when n=1, is

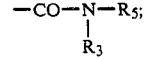

$R_5$ is unsubstituted or substituted phenyl, $C_{1-22}$alkyl, or a 4-(2,2,6,6-tetra-$C_{1-4}$alkyl piperidinyl) group;
$R_6$ is hydrogen, $C_{1-8}$alkyl, $C_{1-8}$ alkoxy, Chd 1-4alkyl monosubstituted by phenyl, or halogen;
$R_7$ is hydrogen;
$R_8$ is $C_{1-22}$alkyl or phenyl ($C_{1-22}$alkyl);
$R_9$ $C_{1-22}$alkyl or $C_{1-22}$alkoxy; and
$R_{10}$ is hydrogen, $C_{1-22}$alkyl or $C_{1-22}$alkoxy.

2. A compound according to claim 1. wherein $R_8$ is $C_{1-22}$alkyl.

3. A compound according to claim 2. wherein $R_1$ is $R_1'$ where $R_1'$ is hydrogen or methyl;

$R_3$ is $R_3'$ where $R_3'$ is hydrogen or methyl;

$R_4$ is $R_4'$ where $R^{4'}$, when $n=2$, is a direct bond and, when $n=1$, is

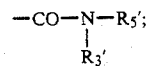

$R_5$ is $R_5'$ where $R_5'$ is $C_{1-22}$alkyl; phenyl unsubstituted or mono-, di- or trisubstituted by groups selected from $C_{1-12}$alkyl, $C_{1-12}$alkoxy and halogen; or a group of the formula

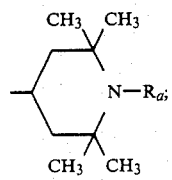

$R_6$ is $R_6'$ where $R_6'$ is hydrogen, methyl, ethyl, octyl, methoxy, ethoxy or chloro;

$R_8$ is $R_8'$ where $R_8'$ is $C_{1-18}$alkyl, $R_9$ is $C_{1-4}$alkyl or $C_{1-4}$alkoxy;

$R_{10}$ is $R_{10}'$ where $R_{10}'$ is $C_{1-8}$alkoxy;

$R_a$ is hydrogen, oxygen, $C_{1-8}$alkyl or $-CO-R_{15}$;

$R_{15}$ is $-C(R_3)=CH_2$, $C_{1-6}$alkyl, $-CO-O-C_{1-4}$alkyl or $-NR_{17}R_{18}$;

$R_{17}$ is hydrogen, $C_{12}$alkyl, $C_{5-6}$cycloalkyl, phenyl, phenyl $C_{1-4}$alkyl, or $C_{1-4}$alkylphenyl; and $R_{18}$ is $C_{1-12}$alkyl of hydrogen.

4. A compound according to claim 2 wherein R is a group of formula IIa.

5. A compound according to claim 2 wherein R is a group of formula IIIa.

6. a compound according to claim 3 wherein R is a group of formula IIa.

7. A compound according to claim 3 wherein R is a group of formula IIIa.

8. A compound according to claim 3 wherein
$R_1'$ and $R_3'$ are hydrogen;
$R_6'$ is $R_6''$ where $R_6''$ is methyl, ethyl or hydrogen;
$R_8$ is $C_{1-12}$alkyl; and
$R_{10}'$ is $R_{10}''$ where $R_{10}''$ is $C_{4-8}$alkoxy.

9. A compound according to claim 8 wherein R is a group of formula IIa.

10. A compound according to claim 8 wherein R is a group of formula IIIa.

11. A compound according to claim 8 of the formula

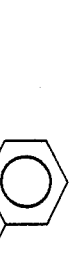

12. A polymeric composition comprising a polymeric material and a light stabilizing-effective amount of a compound according to claim 1.

13. A polymeric composition comprising a polymeric material and a light stabilizing-effective amount of a compound according to claim 2.

14. A polymeric composition comprising a polymeric material having incorporated therein 0.01 to 8% by weight of a compound according to claim 2.

15. A polymeric composition comprising a polymeric material having incorporated therein 0.01 to 8% by weight of a compound according to claim 3.

16. A polymeric composition according to claim 14 in which the polymeric material is selected from the group consisting of polyethylene, polypropylene, ethylene/-propylene copolymers, polyvinyl chloride, polyester, polyamide, polyurethane, polyacrylonitrile, poly(a-crylonitrilebutadiene-styrene), terpolymers of acrylates, styrene and acrylonitrile, styrene/acrylonitrile and stryene/butadiene, polybutylene, polystyrene, chlorinated polyethylene, polycarbonate, polymethylmethacrylate, polyphenylene oxide, polypropylene oxide, polyacetals, phenol/formaldehyde resins, epoxy resins and natural rubber.

17. A polymeric composition according to claim 15 in which the polymeric material is selected from the group consisting of polyethylene, polypropylene, ethylene/-propylene copolymers and poly(acrylonitrile-butadiene-styrene).

18. A lacquer composition based on acrylic, alkyd or polyester resin containing a light stabilizing-effective amount of a compound according to claim 2.

19. A compound of the formula

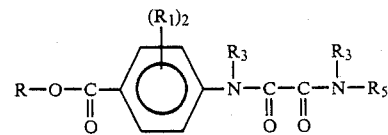

wherein R is a group of the formula IIa and IIIa

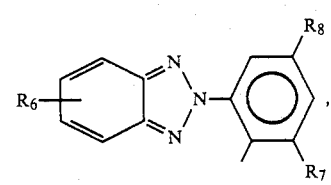

(IIa)

(IIIa)

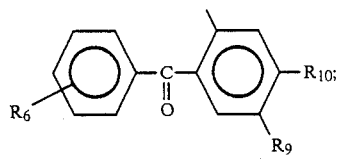

each $R_1$, independently, is hydrogen, $C_{1-8}$alkyl, $C_{1-8}$alkoxy or halogen;
$R_3$ is hydrogen or $C_{1-4}$alkyl;
$R_5$ is a 4-(2,2,6,6-tetra-$C_{1-4}$alkyl piperidinyl) group;
$R_6$ is hydrogen, $C_{1-8}$alkyl, $C_{1-8}$alkoxy, $C_{1-4}$alkyl monosubstituted by phenol, or halogen;
$R_7$ is hydrogen;
$R_8$ is $C_{1-22}$alkyl pr phenyl($C_{1-22}$alkyl);
$R_9$ is $C_{1-22}$alkyl or $C_{1-22}$alkoxy; and
$R_{10}$ is hydrogen, $C_{1-22}$alkyl or $C_{1-22}$alkoxy.

20. A compound according to claim 19 wherein $R_8$ is $C_{1-22}$alkyl.

* * * * *